(12) United States Patent
Tano et al.

(10) Patent No.: US 8,090,447 B2
(45) Date of Patent: Jan. 3, 2012

(54) VISUAL RESTORATION AIDING DEVICE

(75) Inventors: Yasuo Tano, Kobe (JP); Takashi Fujikado, Toyonaka (JP)

(73) Assignee: Nidek Co., Ltd., Gamagori-shi (JP)

( * ) Notice: Subject to any disclaimer, the term of this patent is extended or adjusted under 35 U.S.C. 154(b) by 251 days.

(21) Appl. No.: 11/492,987

(22) Filed: Jul. 26, 2006

(65) Prior Publication Data

US 2007/0027502 A1    Feb. 1, 2007

(30) Foreign Application Priority Data

Jul. 29, 2005   (JP) ................................. 2005-222027

(51) Int. Cl.
*A61N 1/18* (2006.01)
(52) U.S. Cl. .......................................... 607/53; 607/54
(58) Field of Classification Search ............... 607/53, 607/54, 72, 74
See application file for complete search history.

(56) References Cited

U.S. PATENT DOCUMENTS

| | | | | |
|---|---|---|---|---|
| 4,611,596 | A * | 9/1986 | Wasserman | 607/57 |
| 4,664,117 | A * | 5/1987 | Beck | 607/54 |
| 4,803,988 | A * | 2/1989 | Thomson | 607/70 |
| 4,979,508 | A * | 12/1990 | Beck | 607/54 |
| 5,147,284 | A * | 9/1992 | Fedorov et al. | 600/9 |
| 5,411,540 | A * | 5/1995 | Edell et al. | 607/53 |
| 5,935,155 | A * | 8/1999 | Humayun et al. | 607/54 |
| 5,944,747 | A | 8/1999 | Greenberg et al. | |
| 6,658,299 | B1 * | 12/2003 | Dobelle | 607/54 |
| 7,398,124 | B2 | 7/2008 | Fujikado et al. | |
| 7,751,896 | B2 | 7/2010 | Graf et al. | |
| 2004/0102843 | A1 | 5/2004 | Yagi | |
| 2004/0127957 | A1 | 7/2004 | Fujikado et al. | |
| 2004/0176821 | A1 * | 9/2004 | Delbeke et al. | 607/54 |
| 2004/0181265 | A1 * | 9/2004 | Palanker et al. | 607/54 |
| 2004/0193232 | A1 | 9/2004 | Yagi et al. | |

FOREIGN PATENT DOCUMENTS

JP   A-2004-057328   2/2004

(Continued)

OTHER PUBLICATIONS

Dobelle et al. "Phosphenes Produced by Electrical Stimulation of Human Occiptial Cortex, and Their Application to the Development of a Prosthesis for the Blind." J. Physiol. (1974), 243, pp. 553-576.*

(Continued)

*Primary Examiner* — Carl H Layno
*Assistant Examiner* — Allen Porter, Jr.
(74) *Attorney, Agent, or Firm* — Oliff & Berridge, PLC

(57) ABSTRACT

A visual restoration aiding device for restoring vision of a patient, comprises: a signal generation unit including a substrate to be placed on an outer side of a choroid of a patient's eye and a plurality of electrodes arranged on the substrate for applying electrical stimulation pulse signals to cells constituting a retina; a photographing unit which photographs an object to be recognized by the patient; and a processing unit which converts image data obtained by the photographing unit to data for electrical stimulation pulse signal and transmits the converted data to the signal generation unit: wherein, based on the data for electrical stimulation pulse signal transmitted from the processing unit, the signal generation unit forms a waveform of an electrical stimulation pulse signal to be outputted from each electrode into a biphasic rectangular wave including rectangular waves of opposite polarities, and sets a pulse width of the electrical stimulation pulse signal to 0.2 msec. or more and 2 msec. or less.

5 Claims, 10 Drawing Sheets

FOREIGN PATENT DOCUMENTS

| WO | WO 96/39221 | 12/1996 |
|---|---|---|
| WO | WO 99/45870 | 9/1999 |
| WO | WO 02/40095 A1 | 5/2002 |
| WO | WO 02/80828 A1 | 10/2002 |
| WO | WO 02/89912 A2 | 11/2002 |
| WO | WO 2005/000395 A1 | 1/2005 |

OTHER PUBLICATIONS

Japanese Office Action in Japanese Patent Application No. 2005-222027 mailed Feb. 2, 2011 with English-language Translation.

* cited by examiner

| Current Threshold(Perceptual Threshold of Phosphene) | | Color of Phosphene : Green | |
|---|---|---|---|
| | 700 | Number : | 1 |
| | 600 | Shape: | Circle |
| | 700 | | |
| | 600 | | |
| | 900 | | |
| | 800 | Unit: | [µA] |
| Ave. | 716.6667 | | |
| SD | 116.9045 | | |

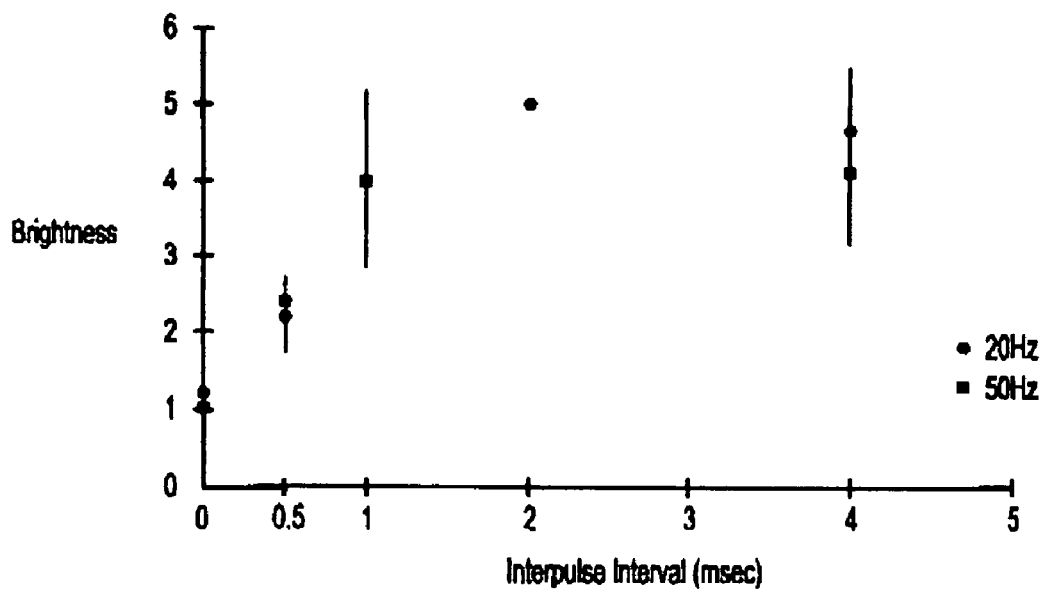
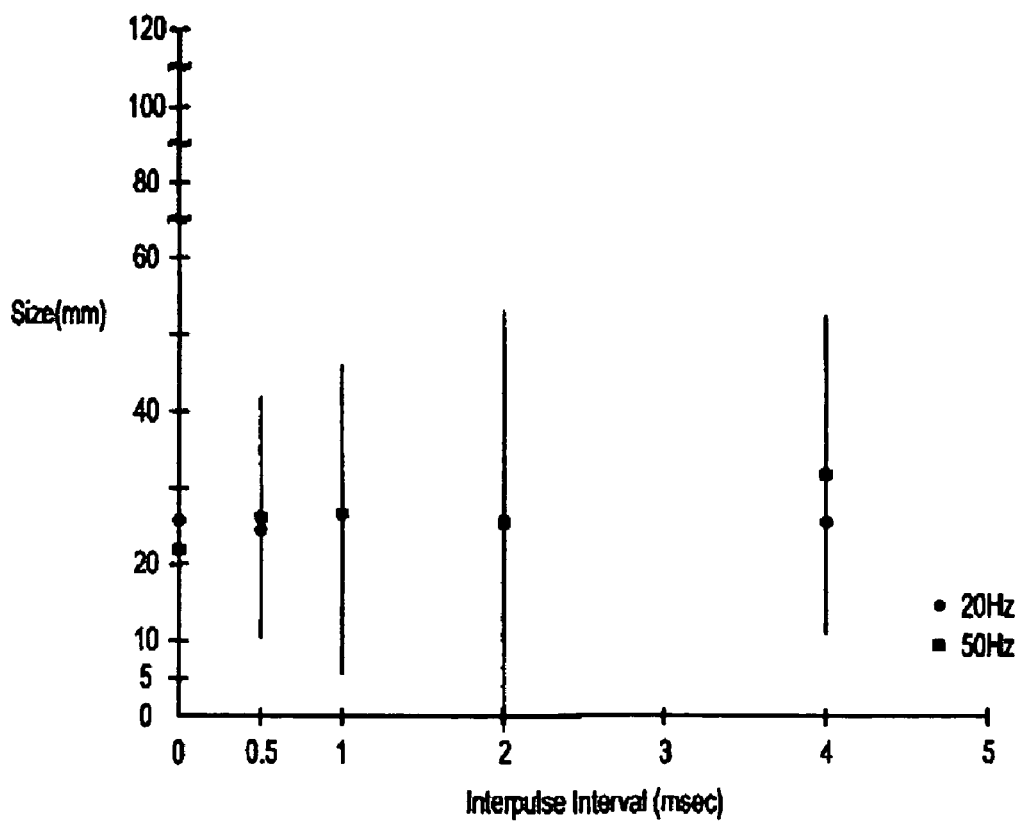

VISUAL RESTORATION AIDING DEVICE

BACKGROUND OF THE INVENTION

1. Field of the Invention

The present invention relates to a visual restoration aiding device for inducing and assisting restoration of vision.

2. Description of Related Art

There have been proposed a visual restoration aiding device for inducing and assisting restoration of vision by applying electrical stimulation (an electrical stimulation pulse signal) to cells constituting a retina from electrodes placed (implanted) in a body (an eye). It has been considered that suitable conditions of the electrical stimulation by such device vary depending on a position in which the electrodes are placed. Accordingly, it has been desired to determine appropriate values of the electrical stimulation pulse signal, e.g. a pulse width and a pulse frequency, according to the electrode placing position.

BRIEF SUMMARY OF THE INVENTION

The present invention has been made in view of the above circumstances and has an object to provide a visual restoration aiding device capable of applying appropriate electrical stimulation for inducing and assisting restoration of vision to cells constituting a retina.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a visual restoration aiding device for restoring vision of a patient, comprising: a signal generation unit including a substrate to be placed on an outer side of a choroid of a patient's eye and a plurality of electrodes arranged on the substrate for applying electrical stimulation pulse signals to cells constituting a retina; a photographing unit which photographs an object to be recognized by the patient; and a processing unit which converts image data obtained by the photographing unit to data for electrical stimulation pulse signal and transmits the converted data to the signal generation unit; wherein, based on the data for electrical stimulation pulse signal transmitted from the processing unit, the signal generation unit forms a waveform of an electrical stimulation pulse signal to be outputted from each electrode into a biphasic rectangular wave including rectangular waves of opposite polarities, and sets a pulse width of the electrical stimulation pulse signal to 0.2 msec. or more and 2 msec. or less.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIGS. 9A and 9B are diagrams showing a relationship between interpulse interval and a phosphene.

DETAILED DESCRIPTION OF THE PREFERRED EMBODIMENTS

Figure 1:
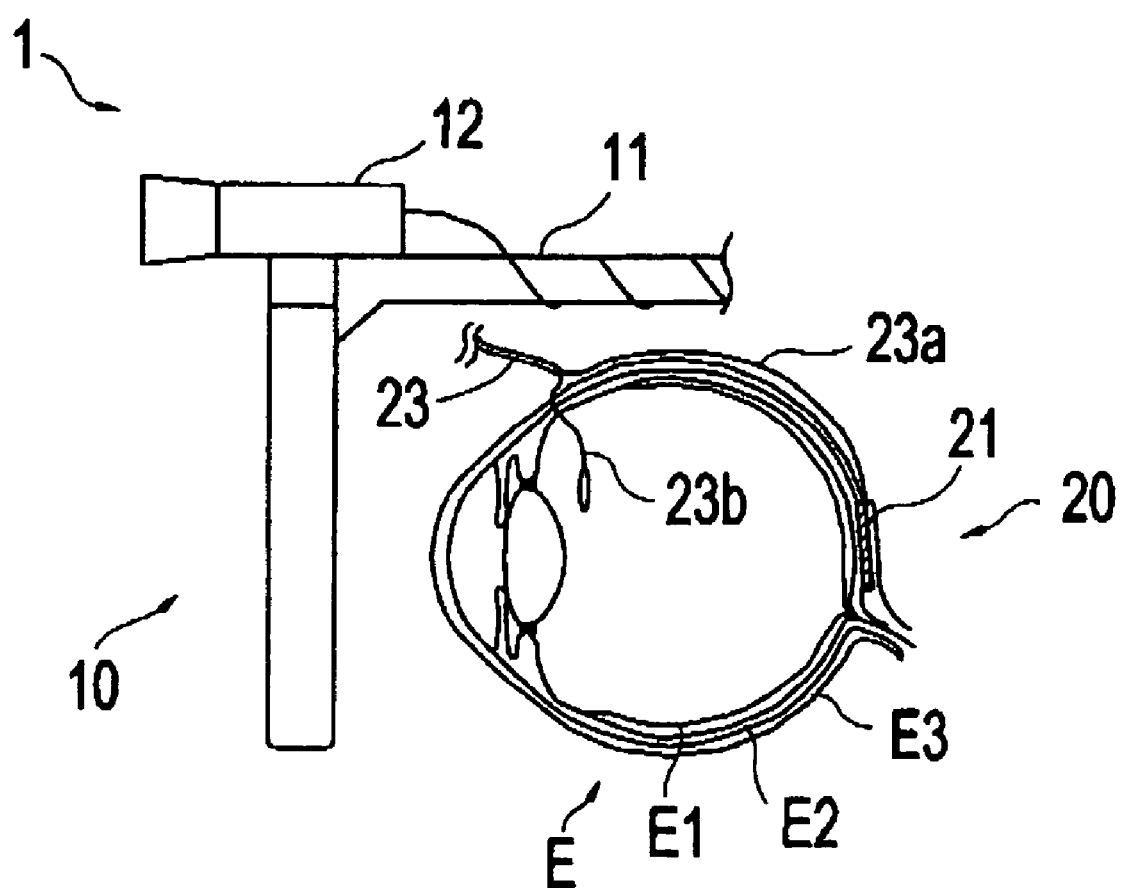
FIG. 1 is a schematic structural view of a main part of a visual restoration aiding device in a present embodiment.
Figure 2:
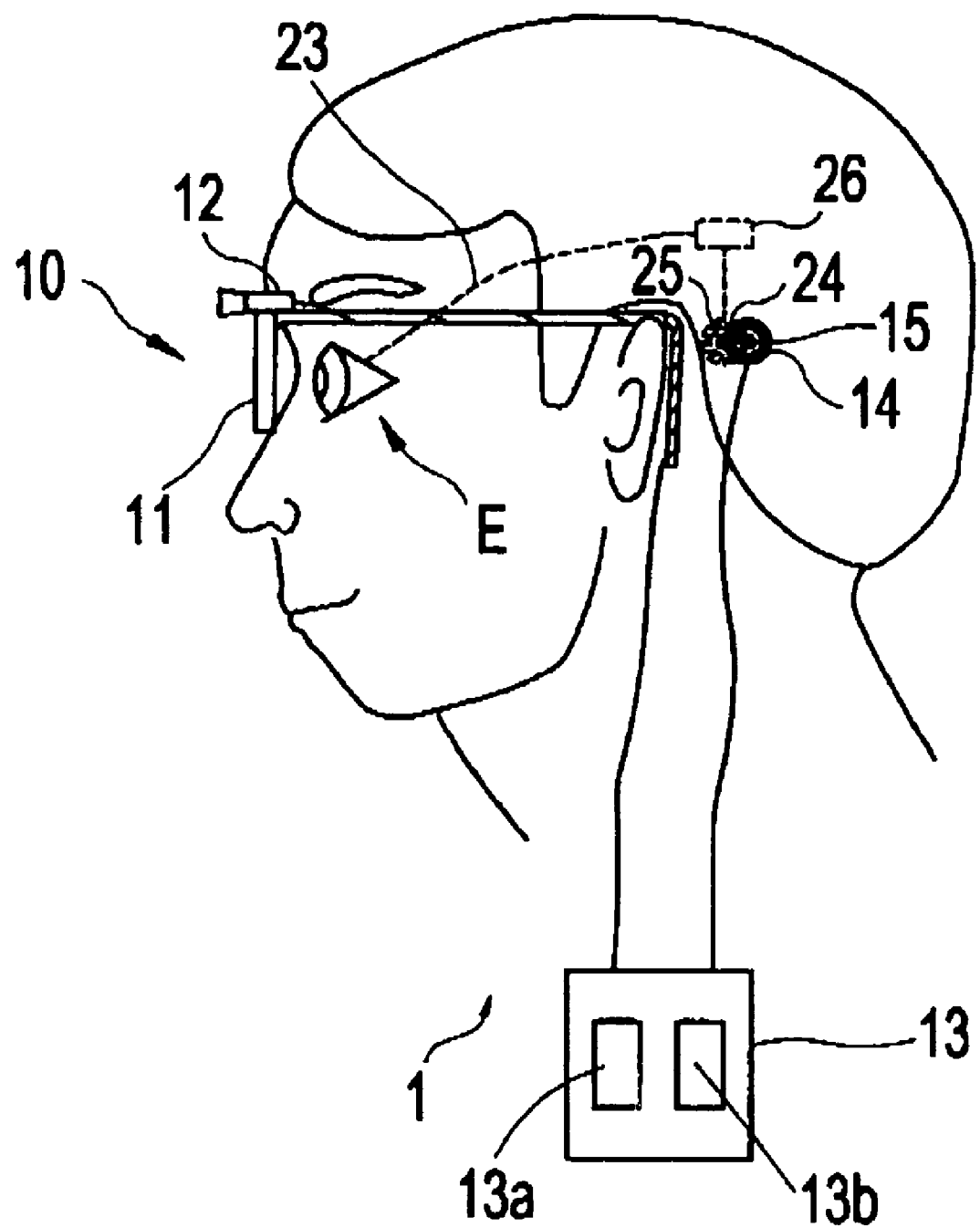
FIG. 2 is a schematic structural view of an external device of the visual restoration aiding device.
Figure 3:
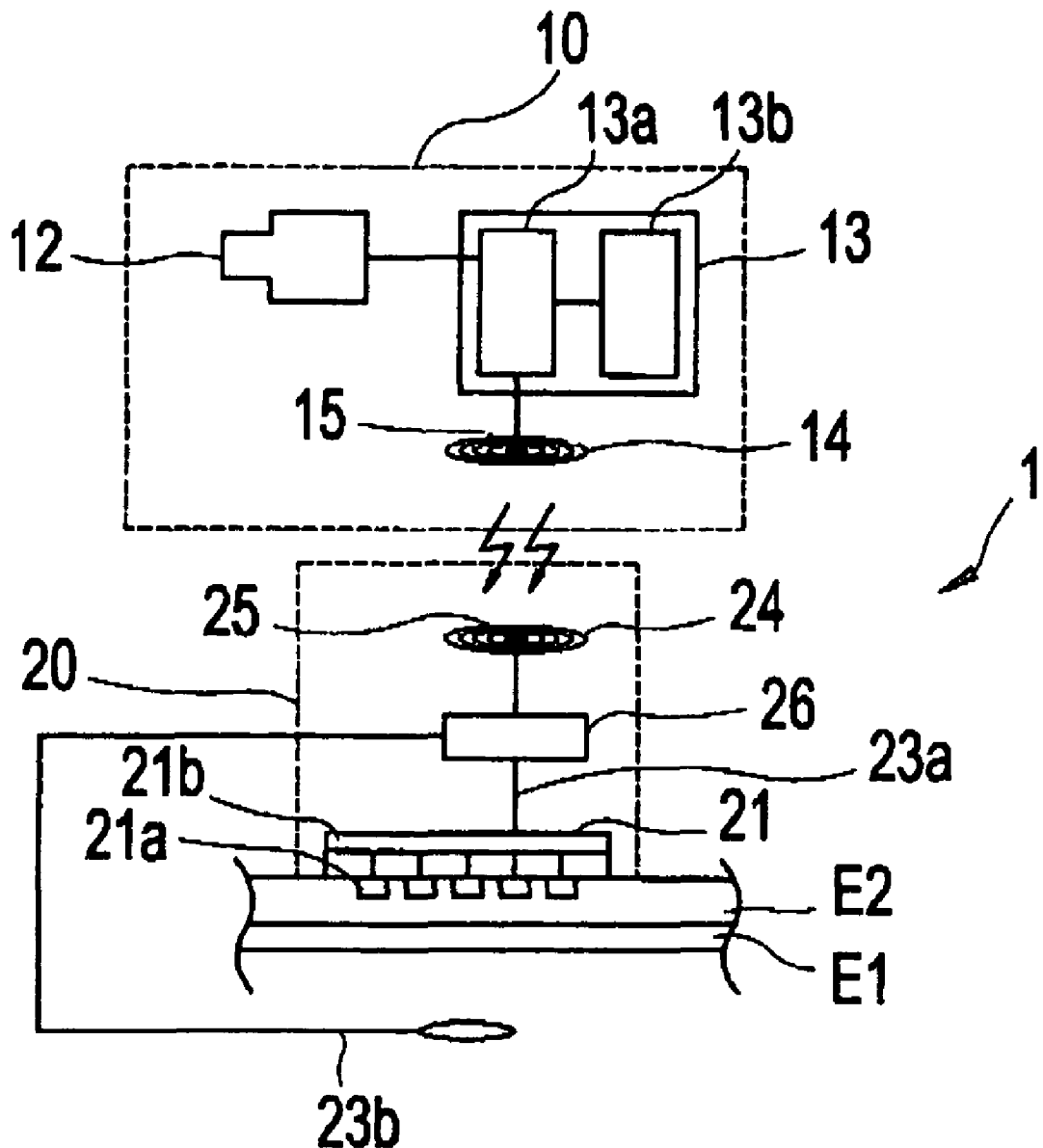
FIG. 3 is a schematic block diagram of a control system of the visual restoration aiding device.

A detailed description of a preferred embodiment of the present invention will now be given referring to the accompanying drawings. FIG. 1 is a schematic structural view of a main part of a visual restoration aiding device in the present embodiment. FIG. 2 is a schematic structural view of an external device of the visual restoration aiding device. FIG. 3 is a schematic block diagram of a control system of the visual restoration aiding device.

A visual restoration aiding device 1 mainly includes an external (extracorporeal) device 10 which photographs the external world, or captures surrounding images, and an internal (intracorporeal) device 20 which applies electrical stimulation to cells constituting a retina E1 to induce and assist restoration of vision. The external device 10 includes a visor 11 which a patient will put on, a photographing unit 12 such as a CCD camera mounted on the visor 11 external unit 13, and a transmitting unit 14 including a primary, coil. The visor 11 is shaped like eyeglasses, which is put on the front of a patient's eye E during use. The photographing unit 12 is mounted on the front of the visor 11 and photographs an object to be recognized by the patient.

The external unit 13 includes a processing unit 13a having a processing circuit and a power supply unit (battery) 13b for power supply to the device 1 (i.e., the external device 10 and the internal device 20). The processing unit 13a makes image processing on image data obtained by the photographing unit 12 and further converts image-processed data to data for electrical stimulation pulse signal. The transmitting unit 14 transmits the data for electrical stimulation pulse signal converted by the processing unit 13a and electric power (data for electric power) from the power supply unit 13b via the processing unit 13a, in the form of electromagnetic waves, to the internal device 20. The transmitting unit 14 is centrally provided with a magnet 15. This magnet 15 is used to enhance data transmitting efficiency of the transmitting unit 14 and to fix the transmitting unit 14 in place relative to a receiving unit 24 which will be mentioned later.

The internal device 20 includes a substrate 21 on which a plurality of electrodes 21a for applying the electrical stimulation to the cells of the retina E1 are mounted (arranged) and which is placed (located) on the outer side of choroid E2 (i.e. between the choroid E2 and sclera E3) of the patient's eye E, a cable 23, the receiving unit 24 including a secondary coil, an internal unit 26, and an indifferent electrode which will be mentioned later. The above components of the internal device 20 excepting the electrodes 21a and the indifferent electrode are covered with a good biocompatible coating agent. The substrate 21 is formed as a thin plate made of a good biocompatible material foldable in a predetermined thickness, such as polypropylene and polyimide.

The receiving unit 24 receives the data for electrical stimulation pulse signal and the data for electric power transmitted from the external device 10. The receiving unit 24 is centrally provided with a magnet 26. This makes it possible to magnetically fix the transmitting unit 14 when placed on a temporal skin of a patient to the receiving unit 24 implanted under the skin. Thus, the transmitting unit 14 is held on a temporal region. The transmitting unit 14 and the receiving unit 24 in the present embodiment are placed on the patient's temporal region, but not limited thereto. It is essential only that these units be able to transmit the data for electrical stimulation pulse signal and the data for electric power from outside to inside the body. For example, an alternative manner is to attach the transmitting unit 14 on the front of the patient's eye E and place the receiving unit 24 in the patient's eye E (e.g. near an anterior segment) so as to face the transmitting unit 14.

The internal unit 26 includes a circuit which divides the signals received by the receiving unit 24 and transmitted through the cable 23 into the data for electrical stimulation pulse signal and the data for electric power, a circuit which converts the data for electrical stimulation pulse signal into an electrical stimulation pulse signal, and others. The internal unit 26 obtains electric power for driving the internal device 20 from the data for electric power received by the receiving unit 24 and transmitted through the cable. This internal unit 26 is also implanted under the patient's temporal skin as well as the receiving unit 24.

The cable 23 includes electric wires 23a and 23b covered with an insulating and good biocompatible material and tied together in a bundle. This cable 23 is arranged under the skin, as shown in FIGS. 1 and 2, to extend along the temporal region from the receiving unit 24 via the internal unit 26 toward the patient's eye E, and along the inner side of an upper eyelid to enter the orbit. The cable 23 in the orbit is divided into the electric wire 23a and the electric wire 23b as shown in FIG. 1. The electric wire 23a is arranged on the outer side (or The inner side) of the sclera E3 and connected to the substrate 21. The other electric wire 23b is arranged penetrating the pars plana of ciliary body so that a tip portion of the wire 23b is placed in the eye E to face the substrate 21, interposing the retina E1 and the choroid E2. The tip portion of the wire 23b is not covered with an insulating material and serves as the indifferent electrode.

The tip portion of the electric wire 23b in the present embodiment is of a ring shape in order to efficiently function as the indifferent electrode, but it is not limited thereto. It may be formed in any shape other than the ring shape or in a simple linear shape. The indifferent electrode in the present embodiment is placed in the eye E, but it is not limited thereto. The indifferent electrode may be placed anywhere only if it can efficiently apply the electrical stimulation pulse signals outputted from the electrodes 21a to the cells of the retina E1. In the present embodiment, further, the tip portion of the electric wire 23b is used as the indifferent electrode. Alternatively, the electric wire 23b and the indifferent electrode may be made as separate parts and, during use, the indifferent electrode is connected with the electric wire 23b. A material for the indifferent electrode may be selected from any materials widely used for electrodes, e.g. gold, silver, and platinum.

The substrate 21 is provided with a plurality of the electrodes 21a for outputting the electrical stimulation, pulse signals to the cells of the retina E1 and a circuit 21b for transmitting the electrical stimulation pulse signals from the internal unit 26 through the electric wire 23a to each electrode 21a. These components form an electrode array serving as a signal generation unit. The internal unit 26 may also be mounted on the substrate 21. A material for the electrode 21a may be selected from any materials widely used for electrodes, e.g. gold, silver, and platinum.

Figure 4A:
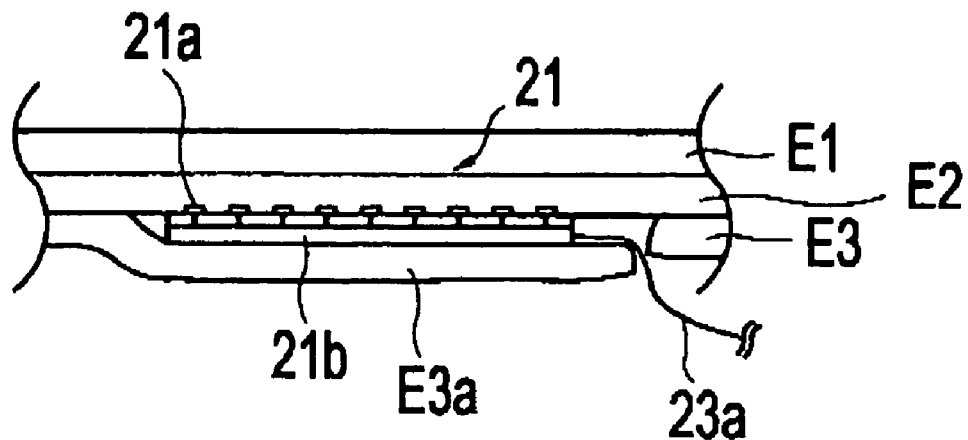
FIGS. 4A and 4B are views each showing a state where a substrate on which electrodes are mounted is placed in a patient's eye.
Figure 4B:
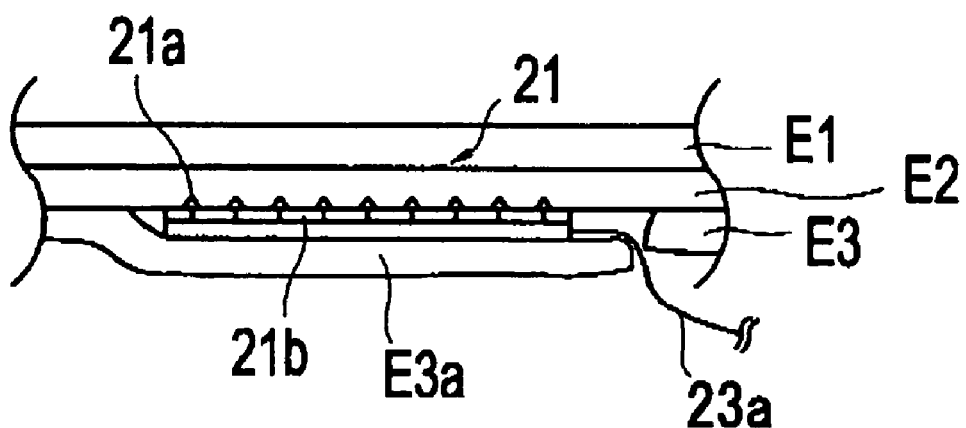

As shown in FIGS. 4A and 4B the substrate 21 is placed between the choroid E2 and the sclera E3 so that the electrodes 21a are in contact with the choroid E2. This placement is performed by incising a part of the sclera E3 to form a sclera flap E3a, opening this sclera flap E3a and putting the substrate 21 therein, closing the sclera flap E3a, and suturing it. Instead of this suturing manner, a bonding manner using a good biocompatible adhesive or another well known manner may be adopted.

Each electrode 21a may be an electrode having a flat surface as shown in FIG. 4A or an electrode having a sharp-pointed surface as shown in FIG. 4B in the side which is brought into contact with the choroid E2.

A technique for placing the substrate 21 is not limited to a sclera fenestration surgery of forming the sclera flap and may be a scleral half-layer incision surgery. In this case, the substrate 21 is placed in a half-layer incised portion of the sclera E3. The substrate 21 is not limited to be placed in contact with the choroid E2 and it may be placed to apply electric stimulation to the cells of the retina E1 from the outer side of the choroid E2 through part of the sclera E3.

The waveform of the electric stimulation pulse signal may be either a monophasic wave or a biphasic wave, but the biphasic wave is preferable for enhancing the safety. This electric stimulation pulse signal is outputted to the cells of the retina E1 to elicit light perception (artificial light perception, intraocular photesthesia) without light stimulus, called "Phosphene", thereby giving artificial vision.

When electrical stimulation conditions (hereinafter, referred to as "electrical stimulation parameters") for allowing a patient to perceive (obtain) an appropriate phosphene are to be determined, the following two points must be satisfied. One is that the electrical stimulation if applied to a human has to be safe, low invasive, and comfortable. Another is that a phosphene caused by one electrode has to be perceived as a bright, small, sharply-outlined spot.

The operations of the visual restoration aiding device 1 having the above structure will be explained below.

Image data obtained by the photographing unit 12 is inputted to the processing unit 13a and is converted into a signal (the data for electrical stimulation pulse signal) of a predetermined band. This signal is then transmitted to the internal device 20 through the transmitting unit 14.

The electric power supplied from the power supply unit 13b is converted by the processing unit 13a into a signal (the data for electric power) of a band different from the data for electrical stimulation pulse signal and is transmitted along with the data for electrical stimulation pulse signal through the transmitting unit 14 to the internal device 20.

The data for electrical stimulation pulse signal and the data for electric power transmitted from the external device 10 are received by the receiving unit 24 and inputted to the internal unit 26 which divides the received data into the data for electrical stimulation pulse signal and the data for electric power. Based on the data for electrical stimulation pulse signal, the electrical stimulation pulse signal is generated.

The electrical stimulation pulse signal from the internal unit 26 is outputted from each electrode 21a placed on the outer side of the choroid E2 (i.e. between the choroid E2 and the sclera E3) through the circuit 21b. At this time, the indifferent electrode has been implanted to face the electrodes 21a, interposing the retina E1 and the choroid E2. Accordingly, the electrical stimulation pulse signal outputted from each electrode 21a can efficiently stimulate the cells of the retina E1, such as bipolar cells and retinal ganglion cells. This enables the patient to recognize the object photographed by the photographing unit 12.

The electrodes 21a in the present embodiment are placed on the outer side of the choroid E2 (i.e. between the choroid E2 and the sclera E3), which is easier than the electrodes are placed on the inner side of the retina E1 (i.e. on the retina E1) or the outer side of the retina E1 (i.e. between the retina E1 and the choroid E2). This is less burden on a patient and an operator. Further, as compared with the case where the electrodes are placed on the inner or outer side of the retina E1, the substrate 21 (the electrode array) can be designed to be larger, thus providing a wider visual field.

To determine the electrical stimulation parameters, several experiments were conducted for the following reasons. Specifically, since the visual restoration aiding device in the present embodiment is structured such that the electrodes which apply electrical stimulation to the cells of the retina are placed on the outer side of the choroid, an experimental system is required to simulate electrical stimulation based on an electric current path from the outer side of the choroid to the retina. In previous researches on the visual restoration, many reports have been presented on experiments for finding electric stimulation parameters suitable for electrical stimulation from mostly the inner side of the retina, but less reports have been presented on experiments on electrical stimulation from the outer side of the retina. In view of this, the applicants conducted experiments to find the electrical stimulation parameters suitable for electrical stimulation from the outer side of the choroid.

Subjects who participated in the following experiments were five normal male adults whose retinas were observed as normal. In five experiments described below, records were made on how they perceived phosphenes. In the following description, the phosphene will be regarded as being caused by electrical stimulation unless otherwise noted.

<Experimental Conditions>

An oxybuprocaine hydrochloride solution (Benoxyl®) was applied to an eye of each subject to give local anesthesia to the surface of an eyeball. Then, an operator opened the eyelid of each subject with an eye-opener. For protection of a cornea, a sodium, hyaluronate and sodium chondroitin sulfate solution (Viscoat®) was applied to the surface of the cornea.

A portion at about 18 mm from the limbus toward the superior temporal quadrant was subjected to stimulation. To expose this portion to be stimulated, each subject was requested to roll his eye downward or inward. An electrode was then attached to the exposed stimulating portion. The electrode was a platinum spherical monopolar electrode (electrode diameter: 1 mm, made by Unique Medical Co. Ltd.). An indifferent electrode was fixed to the back of subject's hand.

When the sclera is pressed by the electrode, each subject perceives a mechanical phosphene. This mechanical phosphene is a phosphene which a person can perceive when his eye is mechanically stimulated from outside by e.g. pressure. Just before application of electrical stimulation, each subject was questioned about in which area of his visual field the mechanical phosphene induced by the pressure of the electrode arose. The experiments were conducted after confirmation that the mechanical phosphene and the phosphene caused by electrical stimulation arose at the same position every stimulation test.

Used as the electrical stimulation pulse signal was a biphasic rectangular wave pulse including rectangular waves of opposite polarities. The polarities of this biphasic rectangular wave pulse were determined so that a first rectangular wave be negative and a second rectangular wave be positive at any time. In some of the experiments, the biphasic pulses were spaced at predetermined intervals (hereinafter, interpulse intervals).

[Evaluation Criteria]

The questions to the subjects were as follows:
(1) The number of phosphenes;
(2) Shape of a phosphene;
(3) Brightness of a phosphene; and
(4) Size of a phosphene.

Regarding the question (1), the subjects perceived one phosphene in every experiment. Regarding the question (2), the subjects perceived a circular phosphene in every experiment.

Figure 5:
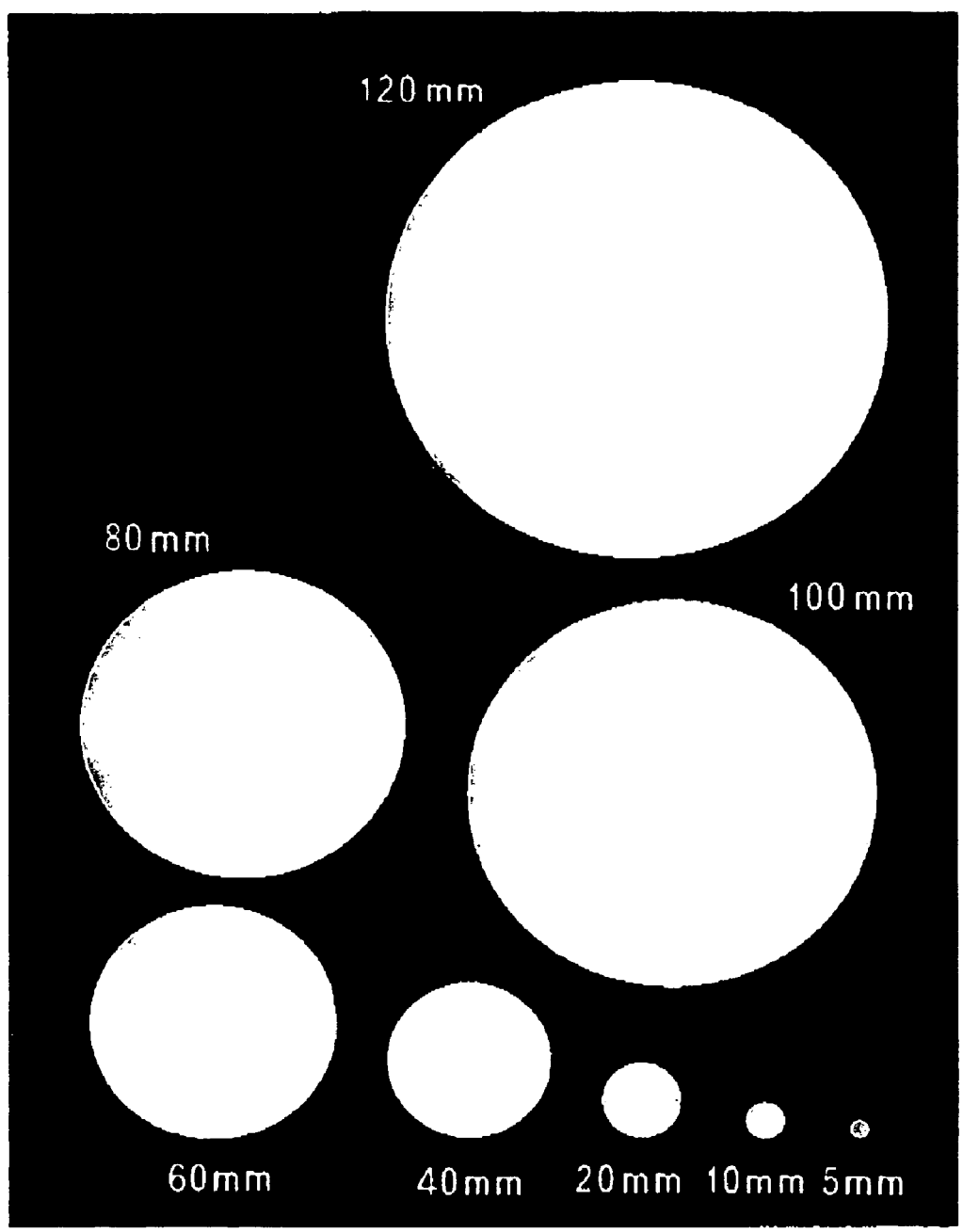
FIG. 5 is a chart in which different-sized circles are formed for comparison and determination of size of a phosphene.

About the question (3), each subject was requested to compare the brightness of a phosphene in the experiments. About the question (4), each subject was requested to compare the size of the perceived phosphene in each experiment with the sizes of circles in a chart (see FIG. 5) formed thereon with various-sized circles, 5 mm to 120 mm in diameter. This chart was disposed at about 10 cm from the subject's eye.

In each experiment, five items listed below were investigated:
1. A relationship between the electric current intensity and a phosphene;
2. A relationship between the pulse width and a phosphene;
3. A relationship between the pulse frequency and a phosphene;
4. A relationship between the interpulse interval and a phosphene; and
5. A relationship between the number of pulse pairs (number of electrical stimulation pulses) and a phosphene.

In each experiment, electric stimulation parameters that each subject perceived (obtained) a suitable phosphene were studied. In each plot related to the following experimental results, a bar represents a standard deviation.

<Experiment 1>

The relationship between the electric current intensity and a phosphene was investigated. The electrical stimulation parameters were set as follows.

Electric current intensity: Variable
Pulse width: 0.5 msec.
Pulse frequency: 20 Hz
Interpulse interval: 0 msec.
The number of pulse pairs: 10 (Stimulation time: 0.5 sec.)

Figures 6A, 6B:
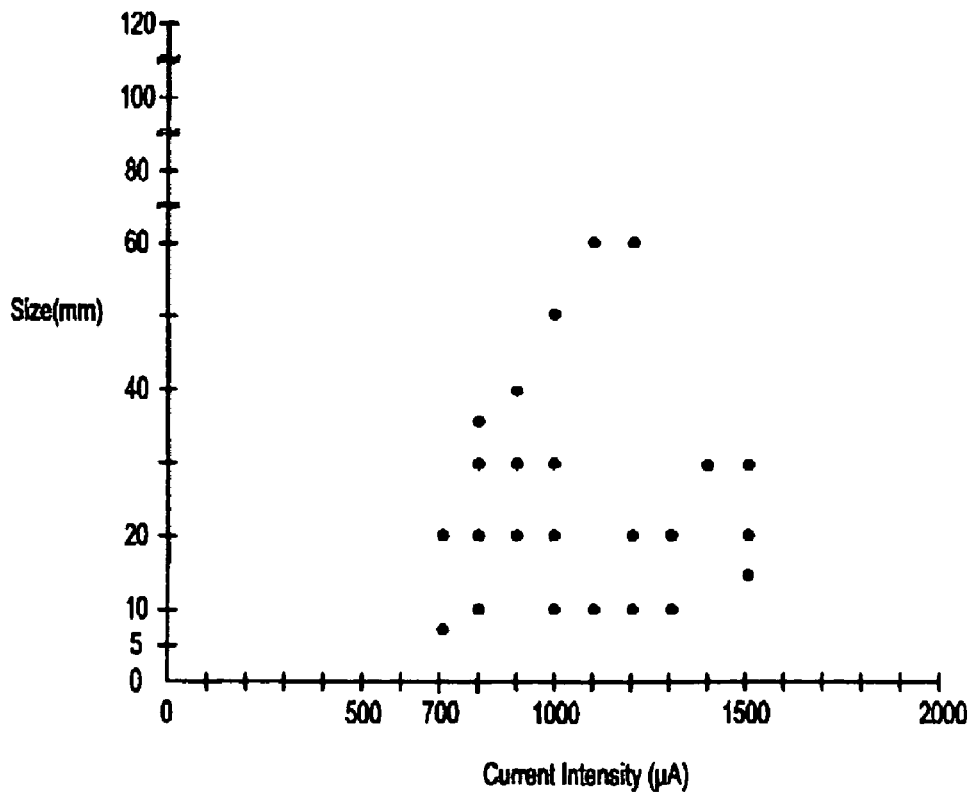
FIGS. 6A and 6B are diagrams each showing a relationship between electric current intensity of an electrical stimulation pulse signal and a phosphene.

FIGS. 6A and 6B show experimental results; FIG. 6A shows minimum electric current intensity (an electric current threshold) at which a phosphene is perceivable, and FIG. 6B shows the relationship between the electric current intensity and the size of a phosphene. In this experiment, the colors of the phosphenes were green. As shown in FIG. 6A, the electric current threshold was set at an average, 716.6667 µA. Further, FIG. 6B shows that there is little difference in size between perceived phosphenes even when the electric current intensity was increased. Accordingly, it was found that each subject begun to perceive a phosphene at an electric current intensity of 700 µA (Electric charge quantity; 350 nC), perceived the phosphene clearly at an electric current intensity of 1000 µA (Electric charge quantity: 500 nC), and perceived the phosphene in a certain size up to an electric current intensity of 1500 μA (Electrical charge quantity: 750 nC).

When the electric charge quantity is below 5 nC, it is difficult to stimulate the cells of the retina such as retinal ganglion cells (Kanda et al. IOVS 45(2), 560-566, 2004). Further, when the electric charge quantity exceeds 750 nC, a living body may be damaged.

From the above results, the electric charge quantity of the electrical stimulation pulse signal to be used in the following experiments was set at 500 nC (Electrical current intensity: 1000 μA). Under this condition, the electrical stimulation parameters that each subject could perceive an appropriate phosphene were investigated.

<Experiment 2>

The relationship between the pulse width and a phosphene was investigated. The electrical stimulation parameters were set as follows.

Electric current intensity; Variable
Pulse width: Variable
Pulse frequency: 20 Hz
Interpulse interval:
The number of pulse pairs: 10 (Stimulation time: 0.5 sec.)

Figure 7A:
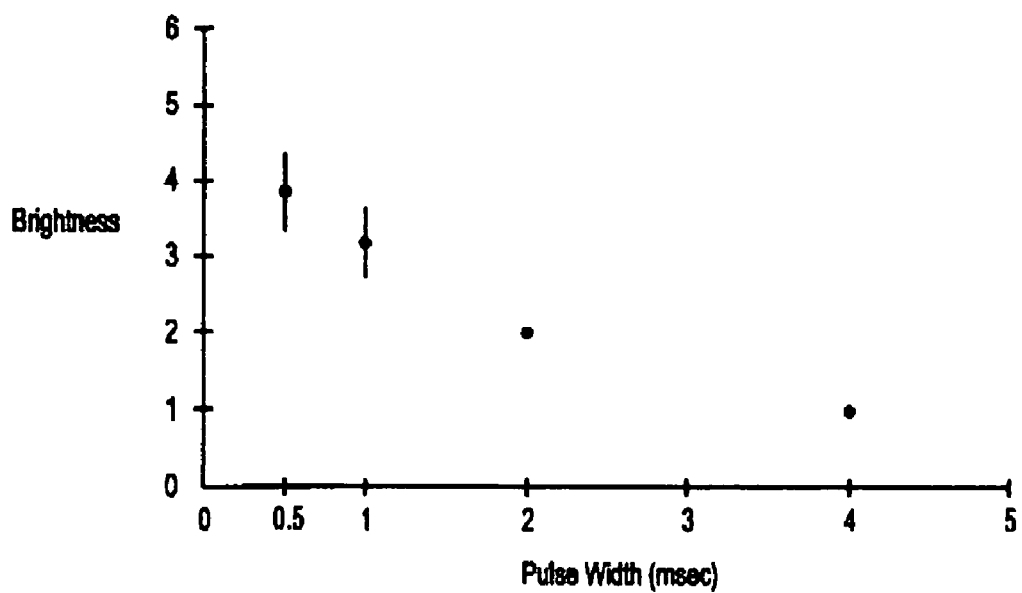
FIGS. 7A and 7B are diagrams each showing a relationship between pulse width of an electrical stimulation pulse signal and a phosphene.
Figure 7B:
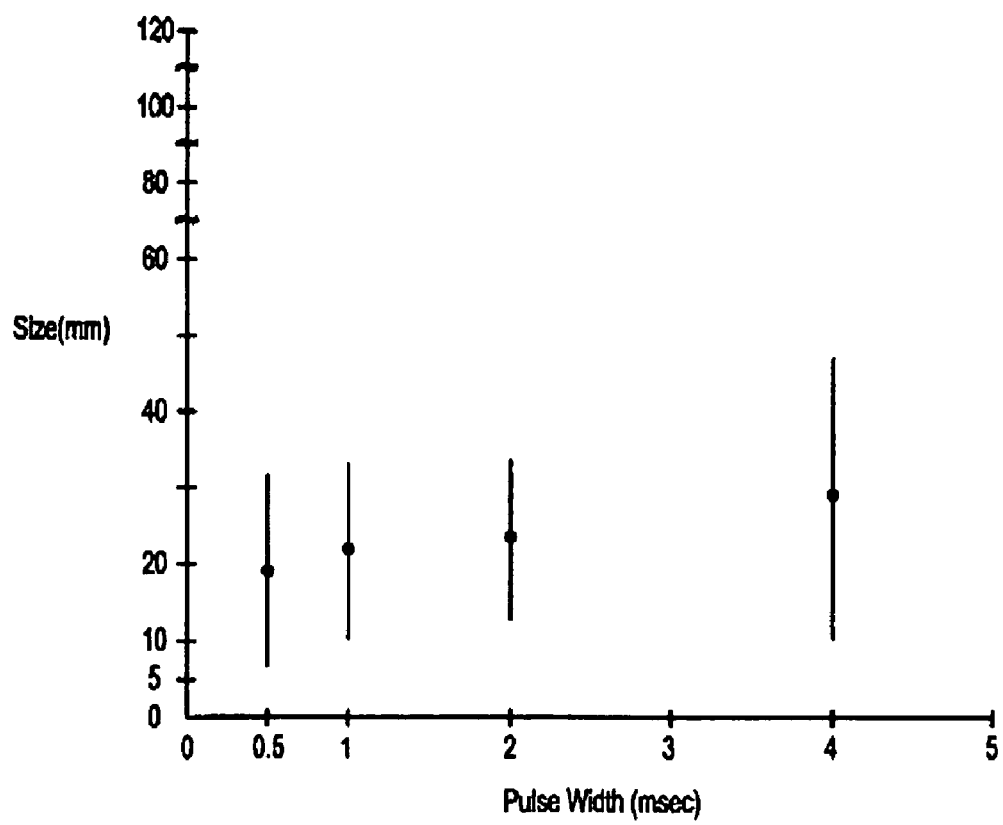

FIGS. 7A and 7B show experimental results; FIG. 7A shows the relationship between the pulse width and the brightness of a phosphene, and FIG. 7B shows the relationship between the pulse width and the size of a phosphene. The relationship between the electric current intensity and the pulse width was adjusted to provide an electric charge quantity of 500 nC. As can be seen in FIG. 7A, the brightness of the perceived phosphene was intense to a degree when the pulse width was 2 msec. or less (to at lowest 0.5 msec.) and that the brightness became more intense as the pulse width was reduced from 2 msec. to 0.5 msec. As can be seen in FIG. 7B, as the pulse width was shorter, the size of the perceived phosphene was smaller.

Further, when the pulse width was reduced to less than 0.5 msec, one subject complained of pain which was likely caused when a phosphene threshold exceeded a pain threshold. Accordingly, the experiments were not conducted under the condition of a pulse width being less than 0.5 msec. It is however conceivable that, in some subjects, a phosphene threshold does not exceed a pain threshold even when a pulse width is 0.2 msec., so that they can obtain phosphenes. For the pulse width of less than 0.2 msec., the stimulation time is too short. This requires a very large electric current to induce a phosphene. On the other hand, the pulse width exceeding 2 msec. is undesirable because it will decrease power efficiency.

From the above results, the pulse width is preferably 0.2 msec. or more and 2 msec. or less, and more preferably 0.5 msec. or more and 2 msec. or less, and most preferably 0.5 msec. or more and 1 msec. or less.

<Experiment 3>

The relationship between the pulse frequency and a phosphene was investigated. The electrical stimulation parameters were set as follows.

Figure 8A:
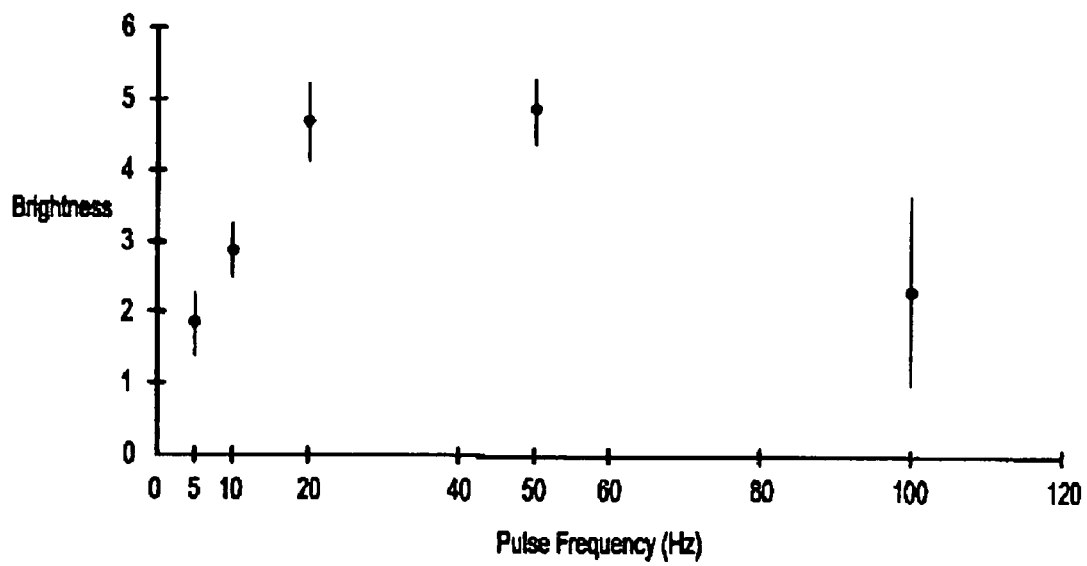
FIGS. 8A and 8B are diagrams showing a relationship between pulse frequency of an electrical stimulation pulse signal and a phosphene.
Figure 8B:
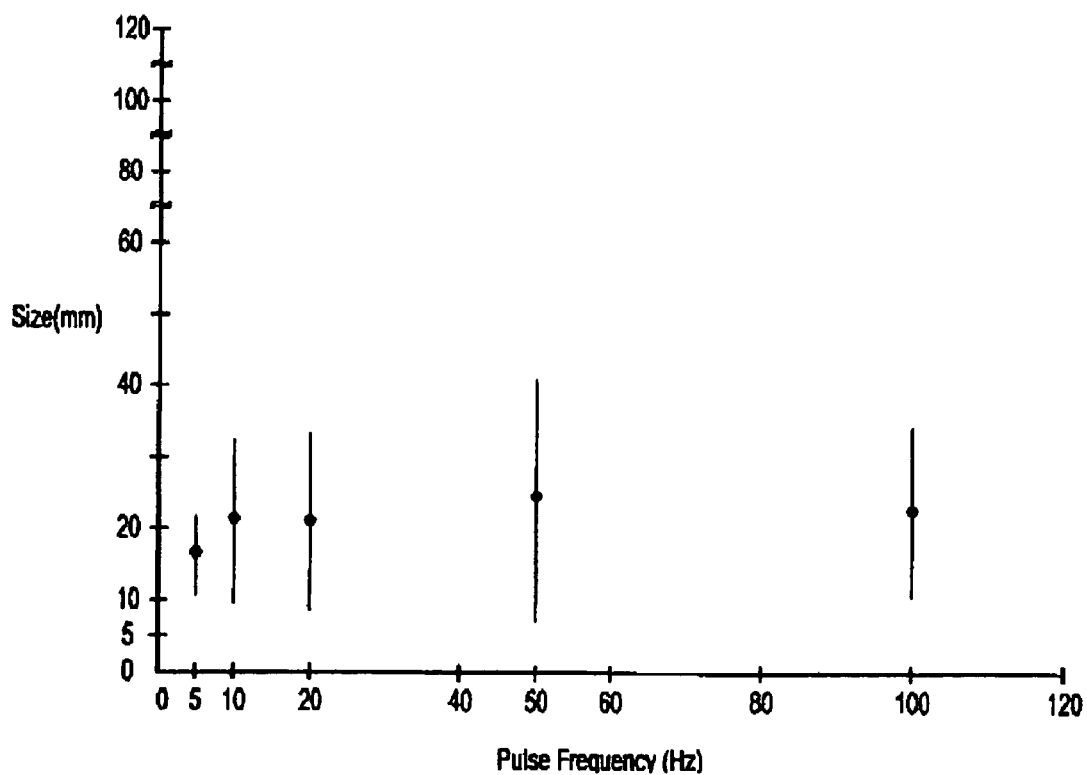

Electric current intensity: 1 mA
Pulse width: 0.5 msec.
Pulse frequency: Variable
Interpulse interval: 0 msec.
The number of pulse pairs: Variable FIGS. 8A and 8B show experimental results; FIG. 8A shows the relationship between the pulse frequency and the brightness of a phosphene, and FIG. 8B shows the relationship between the pulse frequency and the size of a phosphene. The relationship between the pulse frequency and the number of pulse pairs was adjusted to provide a stimulation time of 0.5 sec. For example, the number of pulse pairs was set to 10 with respect to a pulse frequency of 20 Hz and set to 50 with respect to a pulse frequency of 100 Hz. As can be seen in FIG. 8A, the brightness of the perceived phosphene was intense to a degree when the pulse frequency was 5 Hz or more (up to at most 100 Hz) and that the brightness became more intense as the pulse frequency was increased from 5 Hz to 20 Hz. It was further found that each subject perceived a brightest phosphene when the pulse frequency was 20 Hz and 50 Hz respectively. As can be seen in FIG. 8B, no significant difference in size could not be found between perceived phosphenes when the pulse frequency was 10 Hz or more (up to at most 100 Hz).

As the pulse frequency is higher, a switching time of electrical stimulation is shorter (faster), which is preferable in for example a case where an image at a high frame rate is to be, recognized by a patient. When the pulse frequency is too high, contrarily, a patient may perceive a phosphene dark, which is undesirable. Further, power efficiency is also low.

From the above results, the pulse frequency of the electrical stimulation pulse signal is preferably 6 Hz or more and 100 Hz or less, and more preferably 10 Hz or more and 50 Hz or less, and most preferably 20 Hz or more and 50 Hz or less.

<Experiment 4>

The relationship between the interpulse interval and a phosphene was investigated. The electrical stimulation parameters were set as follows.

Electric current intensity: 1 mA
Pulse width: 0.5 msec.
Pulse frequency: 20 Hz and 50 Hz
Interpulse interval; Variable
The number of pulse pairs: 10 (Stimulation time: 0.5 sec.)

FIGS. 9A and 9B show experimental results: FIG. 9A shows the relationship between the interpulse interval and the brightness of a phosphene, and FIG. 9D shows the relationship between the interpulse interval and the size of a phosphene. As can be seen in FIGS. 9A and 9B, the subjects perceived phosphenes irrespective of with or without the interpulse interval. As can be seen in FIG. 9A, the brightness of the perceived phosphene was intense to a degree when the interpulse interval was 0.5 msec. or more (up to at most 4 msec.) and that the brightness became more intense as the interpulse interval was increased from 0.5 msec. to 2 msec. and there was little difference in brightness between 2 msec. and 4 msec. As can be seen in FIG. 9B, there was little difference in size between perceived phosphenes even when the interpulse interval was changed.

When the interpulse interval is too long, one electrical stimulation pulse signal of the biphasic rectangular wave may likely act as two electrical stimulation pulse signals of opposite polarities. Such too-long interpulse interval would lengthen (delay) a switching time of electrical stimulation. This is undesirable in for example a case where an image at a high frame rate is to be recognized by a patient. Phosphenes are perceivable even in the absence of interpulse interval. However, for a patient's eye to which the visual restoration aiding device is actually applied, the electrical stimulation parameter thresholds increase due to diseases of the eye. Accordingly, the interpulse interval is preferably provided for reducing the electrical stimulation parameter thresholds.

From the above results, the interpulse interval of the electrical stimulation pulse signal is preferably 0.5 msec. or more and 4 msec. or less, more preferably 0.5 msec. or more less most preferably 1 msec. or more and 2 msec. or less.

<Experiment 5>

The relationship between the number of pulse pairs and a phosphene was investigated. The electrical stimulation parameters were set as follows.

Figure 10A:
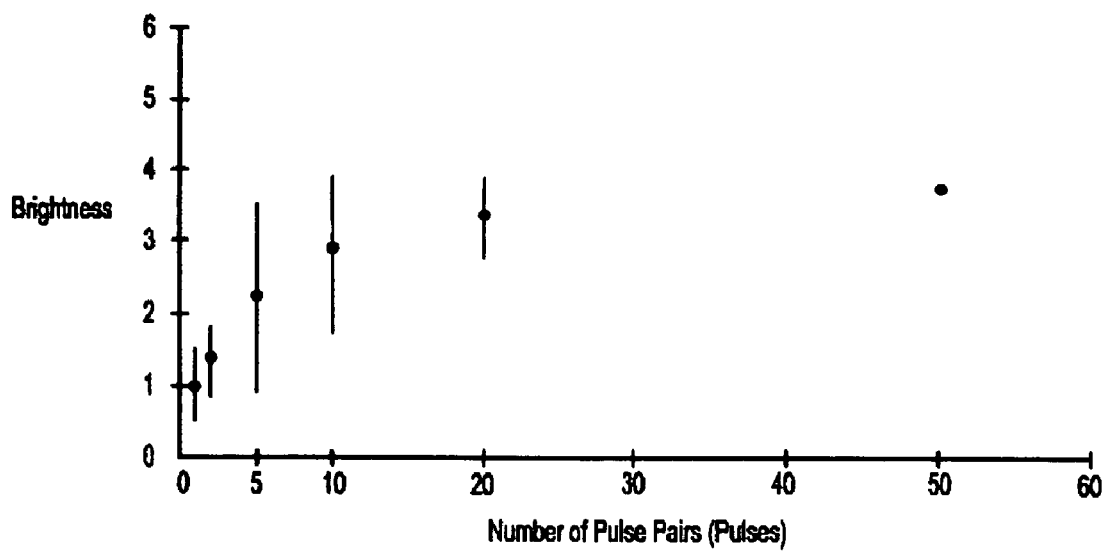
FIGS. 10A and 10D are diagrams showing a relationship between number of pulse pairs and a phosphene.
Figure 10B:
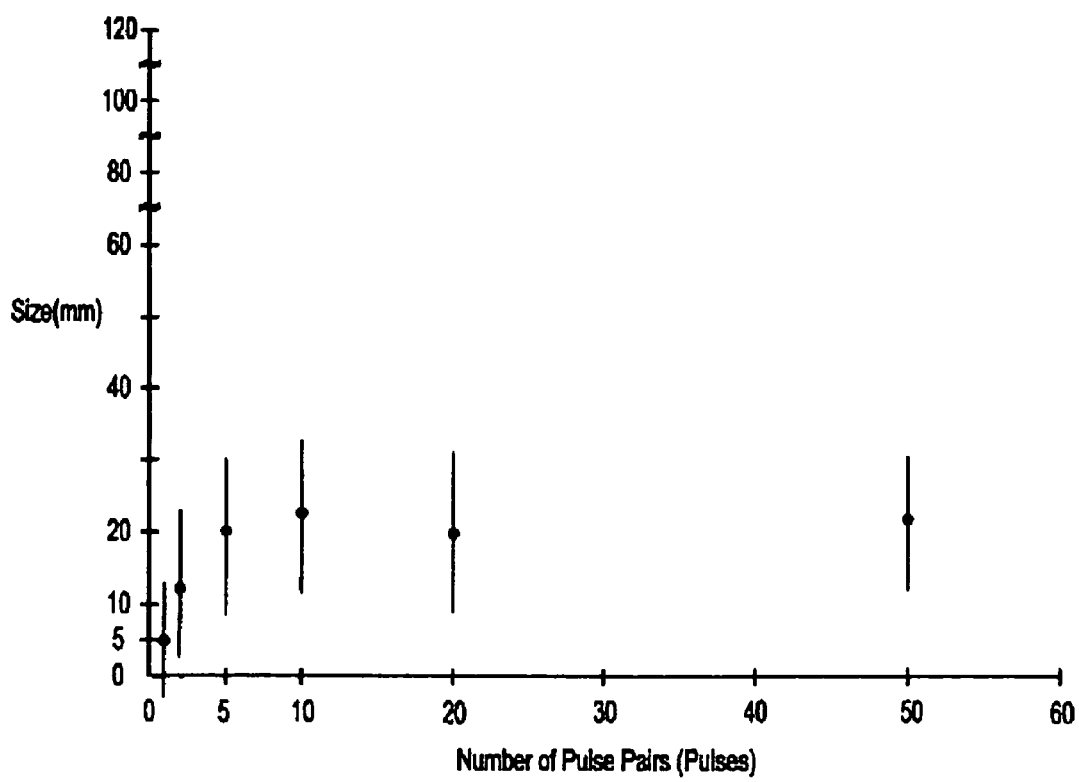

Electric current intensity: 1 mA
Pulse width: 0.5 msec.
Pulse frequency: 50 Hz
Interpulse interval: 2 msec.
The number of pulse pairs: Variable FIGS. 10A and 10B show experimental results; FIG. 10A shows the relationship between the number of pulse pairs and the brightness of a phosphene, and FIG. 10B shows the relationship between the number of pulse pairs and the size of a phosphene. As can be seen in FIG. 10A, the brightness of the perceived phosphene was intense to a degree when the number of pulse pairs was 5 or more (up to at most 50) and that the brightness became more intense as the number of pulse pairs increased from 5 to 20 and there was little difference in brightness between 20 and 50. Further, as seen in FIG. 10B, there was little difference in size between perceived phosphenes when the number of pulse pairs was 5 or more (up to at most 50).

As above, it was found that there is little difference in brightness of perceived phosphenes even if the number of pulse pairs is rather increased. Further, excessive pulse pairs would lengthen (delay) a switching time of electrical stimulation. This is undesirable in for example a case where an image at a high frame rate is to be recognized by a patient. Further, power efficiency is also low.

From the above results, the number of pulse pairs of the electrical stimulation pulse signal is preferably 5 or more and 50 or less, more preferably 5 or more and 20 or less, and most preferably 10 or more and 20 or less.

It is to be noted that a distance between the electrodes and the retina in the above experimental results is different from a distance between the electrodes when actually placed on the outer side of the choroid and the retina. Accordingly, the electric current intensity in the case where the electrodes are actually placed may be set at a smaller value to a degree than the above preferable values determined based on the experimental results in view of the distance between the electrodes and the retina being shorter than that in the experiments.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An electrical stimulation method for restoring vision of a patient, comprising the steps of:
    placing a signal generation unit on an outer side of a choroid of a patient's eye, the signal generation unit including a plurality of electrodes for applying electrical stimulation pulse signals to cells constituting a retina of the patient's eye;
    attaching a photographing unit to the patient for photographing an object to be recognized by the patient; and
    converting image data obtained by the photographing unit to data for electrical stimulation pulse signal by a processing unit and transmitting the converted data to the signal generation unit; and
    outputting an electrical stimulation pulse signal of a biphasic rectangular wave including rectangular waves of opposite polarities from each electrode of the signal generation unit to the cells constituting the retina through the choroid based on the data for electrical stimulation pulse signal transmitted from the processing unit;
    wherein a stimulation condition for generating one phosphene based on the electrical stimulation pulse signal generated from one electrode of the plurality of electrodes is determined such that a pulse width of the electrical stimulation pulse signal is set within a range from 0.2 msec to 1 msec, an electric charge quantity of the electrical stimulation pulse signal is set within a range from 5 nC to 750 nC, an electric current intensity of the electrical stimulation pulse signal is set within a range from 700 µA to 1500 µA, a frequency of the electrical stimulation pulse signal is set within a range from 10 Hz to 50 Hz to generate a phosphene having a diameter ranging from 5 mm to 120 mm as a size of a phosphene to be perceived by the patient without damaging the cells constituting the retina, and the number of pulse pairs of the electrical stimulation pulse signal of the biphasic rectangular wave to be output from one of the electrodes to cause the patient to perceive one phosphene is set to 5 to 50, thereby causing the patient to perceive plural phosphenes to artificially recognize the object photographed by the photographing unit.

2. The electrical stimulation method according to claim 1, wherein the pulse width of the electrical stimulation pulse signal is set to 0.5 msec or more and 1 msec or less.

3. The electrical stimulation method according to claim 1, wherein the pulse frequency of the electrical stimulation pulse signal is set to 20 Hz or more and 50 Hz or less.

4. The electrical stimulation method according to claim 1, wherein an interpulse interval of the electrical stimulation pulse signal is set to 0.5 msec or more and 4 msec or less to generate the phosphenes without damaging the cells constituting the retina, thereby obtaining artificial vision.

5. The electrical stimulation method according to claim 4, wherein the interpulse interval of the electrical stimulation pulse signal is set to 0.5 msec or more and 2 msec or less.

* * * * *